United States Patent [19]
Zafiroglu

[11] Patent Number: 4,897,297
[45] Date of Patent: Jan. 30, 1990

[54] ELASTIC WET COMPRESS

[75] Inventor: Dimitri P. Zafiroglu, Wilmington, Del.

[73] Assignee: E. I. DuPont De Nemours & Co., Wilmington, Del.

[21] Appl. No.: 195,063

[22] Filed: May 17, 1988

[51] Int. Cl.<sup>4</sup> ............................................... B32B 5/16
[52] U.S. Cl. .................................... 428/102; 112/413; 112/420; 428/283; 428/284; 428/286
[58] Field of Search .............. 428/102, 283, 230, 240, 428/243, 248, 254, 284, 286; 604/368, 367, 372, 374; 112/413, 420; 15/208, 209 R

[56] References Cited

U.S. PATENT DOCUMENTS 3,669,103 6/1972 Harper et al. .................. 128/156
3,670,731 6/1972 Harmon ......................... 128/284
4,654,039 3/1987 Brandt et al. .................. 604/368

Primary Examiner—Marion C. McCamish

[57] ABSTRACT

An article of manufacture is provided that is especially suited for use as a hot or wet compress. The article has two outer layers at least one of which is an elastic, water-permeable fabric. The outer layers surround a particulate filling material which is made of 5–30% of a super-absorbent polymer and 70–95% of diluent.

7 Claims, No Drawings

ELASTIC WET COMPRESS

BACKGROUND OF THE INVENTION

1. Field of the Invention

This invention relates to an article of manufacture that is especially suited for use as a hot or cold wet compress. In particular, the invention concerns such an article that is stretchable and conformable and contains a hydrogel-forming polymeric material.

2. Description of the Prior Art

Hot or cold compresses for medical or veterinary uses are usually in the form of wet fabrics, such as towels or bandages, or impermeable waterproof containers, such as packs, hot water bottles, hot water bladders, etc. Although hot or cold wet fabrics conform to the surface they cover, the fabrics hold little water, must be changed frequently and allow water to escape when the wet fabric is compressed. Impermeable waterproof containers, on the other hand, are not very conformable, because they usually are made of thick and tough materials in order to hold water. Often, the water or ice in these impermeable containers moves and accumulates in spots where it is not needed. Most of the known compress devices also significantly restrict the mobility of the user, especially when the compress is applied against a flexing part of the body, such as an arm, elbow, knee, neck, etc. Most of the impermeable containers are applied over bandages, gauze, towels, underwear, and the like because the containers can cause discomfort when directly applied against the skin.

Maintaining the proper moisture balance on surfaces, such as healing skins of humans, animals and plants, requires extensive care, remoistening, or exposure to controlled humidity conditions. The present inventor is unaware of any compress that contacts the skin, is conformable and still has a sufficiently large reservoir of moisture to be useful for long periods of time. Moreover, no compress of very high conformability suitable for irregular surfaces is known.

Although not concerned with wet compresses per se, U.S. Pat Nos. 4,654,039 (Brandt et al), 3,670,731 (Harmon) and 3,669,103 (Harper et al) disclose absorbent polymeric particles of hydrocolloidal polymers, often referred to in the trade and hereinafter as "super-absorbent polymers", which can be mixed with various fibrous or pulp materials to provide absorbent fillers for disposable diapers, sanitary napkins, paper towels, incontinent pads, facial tissues and the like. These polymers, when wetted with water, form hydrogels.

The purpose of the present invention is to provide an article of manufacture that can be used as a highly conformable, flexible, well-fitting, long-lasting medical or veterinary wet compress or bandage, which can readily absorb and retain large amounts of water.

SUMMARY OF THE INVENTION

The present invention provides an article of manufacture that is especially suited for use as a wet compress. The article has an upper and a lower outer layer. Contained between the outer layers is a particulate filling material that consists essentially of a super-absorbent polymer amounting to 5 to 30 percent, preferably 8 to 15%, of the total weight of the the filling material, with the reminder of the filling material being a solid diluent. At least one of the outer layers is an elastic, water-permeable fabric that has a recoverable stretch of at least 50% in at least one direction, preferably 100 to 300%. A preferred elastic fabric has a bendability of no greater than 1¼ cm, most preferably, no greater than ¾ cm.

DETAILED DESCRIPTION OF PREFERRED EMBODIMENTS

The article of manufacture of the present invention is flexible, elastic and highly conformable to the surface to which it is applied. It is capable of keeping intimate contact with irregular and moving surfaces. The article is capable of holding large quantities of water per unit weight of filling material. The filler material can absorb 15 to 35 times its own weight in water to form a hydrogel. In so doing the article can swell to 3 to 10 times its dry volume. Because of these characteristics and the water-permeability of the elastic outer layer, the article can provide a moisture-balancing effect to the surface to which it is applied. Accordingly, the article is especially useful for medical bandages in the treatment of burns and as a wet compress in general. The wet article may also be used for wrapping cut tree trunks, for beauty care and the like.

The upper and lower outer layers of the article of manufacture of the present invention may be of the same or of different materials. However, at least one of the layers is a water-permeable, elastic fabric. Generally, the elastic fabric has a recoverable stretch of at least 50% in at least one direction. Preferably such recoverable stretch is in the range of 100 to 300%. Below a recoverable stretch of 50%, the fabric lacks the ability to accommodate the large increase in volume associated with the swelling of the filling material as it absorbs water and becomes a hydrogel. The elastic water-permeable fabric is also conformable, as indicated by a "bendability" of no greater than 1¾ cm, preferably no greater than ¾ cm.

Bendability is determined by placing a 10-inch (25.4-cm) long by 1-inch (2.54-cm) wide strip of fabric sample flat on the horizontal surface of a platform that forms a right angle edge having a 1/16-inch (1.59 mm) radius between the horizontal and vertical planes of the edge. The sample is advanced over the edge of the platform until a 6-inch (15.2-cm) length of the sample extends over the edge. A weight is placed atop the 3 inches (10.2 cm) of the strip starting from the end of the horizontal portion. The bendability is defined as the distance between the unsupported extended end of the strip to the vertical edge of the platform. As reported herein, the bendability is the average of five measurements for each fabric.

Preferred water-permeable elastic fabrics for use in the present invention are stitch-bonded fabrics in which the stitching thread is an elastic thread, such as a nylon-covered spandex thread. The substrate to which the elastic thread is multi-needle stitched is preferably a spunbonded polyolefin fabric, such as the spunbonded polypropylene fabric of Example 1 below, or a carded batt of staple fibers, such as the batt of acrylic and polyester staple fibers of Example 2 below. The stitch-bonding may be performed on conventional "Mali" or "Liba" multi-needle stitching machines, such as those disclosed by Bahlo, "New Fabrics without Weaving" Modern Textiles Magazine, November 1965, pages 51-54.

Other elastic water-permeable fabrics suitable for use in accordance with the present invention can be made of natural or synthetic fibers which contain a sufficient number of elastic fibers to meet the elastic recovery requirements set forth for the outer layer of the article of manufacture. In addition to nonwoven fabrics, knitted or woven fabrics containing elastic yarns (e.g., ½-10% by weight of spandex threads) can be employed. For special purposes, the water-permeable elastic fabric may coated.

Particulate filler material suitable for use in the article of manufacture of the present invention consists essentially of super-absorbent polymer amounting to 5 to 30%, preferably 8 to 15%, of the total weight of the filling material. Super-absorbent polymer concentrations of less than 5% are avoided because at such concentrations, the article of manufacture would have inadequate water-holding capacity and may not form a hydrogel. Concentrations of super-absorbent polymer of greater than 30% are avoided because at such high concentrations the filling material does not wet uniformly, may even block after absorbing but a small amount of water, and its water-holding capacity per unit weight starts diminishing with further increases in concentration. The remainder of the particulate filling material is a diluent, preferably in the form of a mixture of a synthetic polymer pulp and wood pulp.

Super-absorbent polymeric materials, which when wetted with water form hydrogels, are disclosed in Harmon, U.S. Pat. No. 3,670,731, Brandt et al, U.S. Pat. No. 4,654,039 and Harper et al, U.S. Pat. No. 3,669,103, the entire disclosure of which are hereby incorporated herein by reference. The super-absorbent polymeric materials generally are composed of water-insoluble hydrocolloidal particles having from about 25 to 72% of their molecular structure composed of hydrophilic groups. The super-absorbent polymer usually has been crosslinked to introduce a limited water insolubility into the molecule. Suitable water-insoluble hydrocolloid absorbent materials have a minimum average molecular weight per crosslink of about 13,000 and a maximum molecular weight per crosslink of about 276,000. In general, the extent of crosslinking is limited so that the polymeric network of the hydrocolloid is not soluble in water, yet remains flexible and swells as aqueous liquid is absorbed within its structure. As the hydrocolloid swells it absorbs 15 to 35 times, sometimes as much as 70 times, its own weight in water, but maintains the approximate shape and geometry it had before contact with the water.

In accordance with the present invention, the particulate super-absorbent material can be in the form granules, flakes, thin film particles, cellular foam pieces, short fibers coated with the polymer, or the like. Granules are preferred because these are easiest to mix with the diluent particles and have a very large surface area available for absorbency. As the particulate, water-insoluble hydrocolloid accepts liquid it substantially immobilizes the liquid inside its structure, and the resulting particulate, liquid-swollen structure is gelatinous and referred to herein as a hydrogel. The particles of super-absorbent polymer can be dried or dehydrated by conventional means and returned to approximately their original size. Then the particles can again operate as before to absorb and bind aqueous liquids.

The ability of the super-absorbent polymeric material to swell in the presence of water is important to this invention. Swelling fills the article of manufacture and provides shape and conformability to the product. Those hydrocolloid compounds which have been ir-radiation-crosslinked to significantly reduce the swelling are not satisfactory for use in the present invention.

Depending on economics and anticipated number of uses, the diluent may include synthetic textile fibers, wood pulp fibers, cotton linters, and mixtures of such fibers. The diluent may also be a granulated solid, such as ground polystyrene foam. A preferred diluent is a mixture of wood pulp and polyethylene synthetic pulp, as disclosed in the examples below. It is believed that the diluent prevents packing of the hydrocolloidal material and ensures that all of the hydrocolloidal material is available to absorb water.

The completed article of manufacture of the invention is flexible, elastic and conformable. The water-permeable elastic layer can absorb, adsorb or otherwise allow water to pass through the layer to the super-absorbent material. The article can have any desired shape or form, such as a pillow, tube, quilt, or the like. The hydrogel formed when water enters the article of manufacture of the invention is substantially contained within the device and does not leak out easily. Some water can evaporate slowly from the article during use. However, the article may then be rewetted to assure that the full capacity of the filling to absorb water is employed, or if desired totally dried and re-used at a later time.

EXAMPLE 1-2

These examples illustrate preparation of two articles of the invention and show the advantageous properties of the articles for use as wet compresses. The two samples of the invention differ in the elastic, water-permeable fabric employed to provide the outer layers of the article.

For the first sample, the water-impermeable elastic layer was prepared from a 1.25-oz/yd$^2$ (42.4-g/m$^2$) spunbonded sheet of 1.5-dpf (1.65 dtex) polypropylene fibers, purchased from Waynetex, Inc. of Waynesboro, Va. The sheet was stitch-bonded with a 3.5-meter-wide two-bar "Liba" stitchbonder, which laid-in, a yarn of 20-dpf (22 dtex) "Lycra" spandex (manufactured by E. I. du Pont de Nemours and Company) covered with 20-dpf (22-dtex) nylon filament on a tricot pattern with 14 stitches per inch (5.5 stitches/cm) across the machine. The covered spandex yarn was secured with a chain-stitched 40-dpf (44-dtex per filament) polyester filament thread, also stitched at 14 stitches per inch (5.5 stitches/cm). All stitch lengths were 2.5 millimeters. A 46-inch long by 24-inch wide (113×59 cm) sample was prepared. The sample was then washed in water at 160° F. (71° C.) containing an industrial detergent. The fabric shrank to 20 by 20 inches (49×49 cm) and became soft, conformable and elastic. The bendability of the fabric measured only 0.1 inch (0.25 cm) in the length direction and 0.4 inch (1.1 cm) in the width direction. After shrinking, the fabric weighed 3.9 oz/yd$^2$ (132 g/m$^2$). The fabric exhibited a recoverable stretch of greater than 150%.

A second water-permeable elastic fabric was prepared by stitch-bonding a carded batt. The batt was prepared by carding a together 75% of 3.3 dtex T-72 "Orlon" acrylic staple fibers and 25% of 3.3 dtex "Dacron" T-262 polyester staple fibers (both sold by E. I. du Pont de Nemours and Company) on a Hergeth Dual Card. The length of the staple fibers averaged 1½ inches (3.8 cm). The batt weighed 2-oz/yd$^2$ (68 g/m$^2$). The batt was lightly bonded with a Kusters Bonder operating at a temperature of 140° C. with a patterned bonding roll that had 6.3 points/cm in the length and width directions, each point being 0.030 inch (0.07 cm) in diameter. After bonding, the batt was stitch-bonded with the same spandex-containing yarn as was used for the fabric described in the preceding paragraph. A multi-needle stitching machine of the type disclosed by Zafiroglu, U.S. Pat. No. 4,704,321, Example 1, the disclosure of which is hereby incorporated herein by reference, was employed to provide a tricot-stitch pattern with 12 stitches/inch (4.7 stitches/cm). The elastic fabric was 0.13 cm thick and contained less than about 1% of spandex fibers. The fabric was heat treated in an unrestrained condition for 30 minutes in an oven operated at 100° C. The fabric exhibited a bendability of less than 0.7 cm in both the length and width directions and a recoverable stretch of greater than 110% and greater than 40% in the length and width directions respectively.

Each of the above-described fabrics was employed for the upper and lower layers of an article of manufacture made in accordance with the invention. The articles made with the first of the above-described elastic fabric were designated samples of Example 1 and those made with the second of the above-described elastic fabrics were designated samples of Example 2. The same hydrogel-forming filling material was used for each sample of Examples 1 and 2. The filling material consisted of 40% wood pulp, 50% "Tywik"-ST and 10% Superabsorbent Polymer Powder, which were blended together in a laboratory Waring blender operated for 10 minutes at 800 rpm. The wood pulp had been prepared earlier from 1.3-oz/yd$^2$ (44.1 g/m$^2$) commercial Western Red Cedar paper (obtained from the Allied Paper Co., Kalamazoo, Mich.), which had been was run through a paper shredder, then opened on the same Waring blender at 800 rpm for 15 minutes. The "Tywik-ST" polyethylene pulp (obtained from E. I. du Pont de Nemours and Company) was prepared by the method in which a nonbonded sheet of plexifilamentary polyethylene strands of flash-spun, oriented film fibril elements was cut into small pieces, reduced in size by in a Turbo-mill and then treated with "Miranol" C2M-SF surfactant to provide 2% surfactant in the resultant polyethylene pulp. "Miranol" is an derivative of coconut acid sold by ranol, Inc. of Dayton, N.J. The super-absorbent polymer powder was "Water Lok" Superabsorbent Polymer J-500, sold by the Grain Processing Group of Muscatina, Iowa.

A 45-gram weight of the filling material blend of the preceding paragraph was spread evenly over a 12-inch by 12-inch (30.5×30.5 cm) area between two sheets of each of the above-described elastic water-permeable fabrics. A ½-inch (1.3-cm) wide strip in the middle was left empty of filling material. The perimeter and the empty strip along the middle were thermally sealed with a ¼-inch (0.64-cm) wide hot bar to create two 6 inch by 12 inch (15.2×30.4 cm) chambers, each containing 22.5 gms of the blend. The product was capable of being stretched freely along the length of the seals. The thusly formed article was 0.20-inch (0.51-cm) thick and weighed a total of 72 gms (i.e., 45 grams of blend and 27 grams of fabric). Two additional articles were formed and sealed in the same manner but contained no filling. These empty articles were used as control samples.

The article made with the first water-permeable elastic fabric described above (Example 1) was dipped in ice-water for one minute. It absorbed and retained 1535 grams of water. Redipping in ice water for two more minutes did not change the amount of water absorbed. The empty replica of the device absorbed only 60 grams of water. Thus, the filling was calculated to have absorbed 32.2 times its weight in water. After thoroughly squeezing the article by hand, the weight of water was decreased to 1218 grams or 16.7 times the weight of the weight of the filling material. With this amount of water, the dimensions of the device had changed from 0.20×12×12 inches (0.51×30.5×30.5 cm) when dry to 1.50×14×12.5 inches (3.8×35.6×31.8 cm) when wet. This corresponded to a volume increase by a factor of 9.1. The article was placed flat on a 8-mesh/inch, 72%-open-area screen. A 160-lb (72.7 kg) weight supported by a 12×12 inch (30.5×30.5 cm) steel plate was placed on the wet article and left in place for 60 minutes. No gel escaped from the article, no water loss could be measured and the dimensions of the article did not change.

Similar results were obtained with the article made with the second elasticwater-permeable fabric described above (Example 2).

After re-soaking the sample of Example 1 in ice-water and squeezing out excess water, a thermocouple was placed between the sample and a ⅛-inch (0.32-cm) thick plate of "Lucite". The sample and the plate were placed on the surface of the table with the top of the plate exposed to room air. Air temperature was 70° F. (21° C). The thermocouple was placed in the center of one of the 6-by-12 inch (15.3×30.5 cm) sections. The following temperatures were recorded:

| Time | Temperature | |
| --- | --- | --- |
| | °F. | °C. |
| 0 | 33 | 0.6 |
| 1 minute | 35 | 1.7 |
| 30 minutes | 35 | 1.7 |
| 1 hour | 35 | 1.7 |
| 2 hours | 35 | 1.7 |
| 3 hours | 36 | 2.2 |
| 4 hours | 36 | 2.2 |
| 5 hours | 46 | 7.8 |
| 8 hours | 58 | 14.4 |

These data indicate that the wet article has a very high heat capacity and a high insulative value. The weight of the device during the eight hours of test had decreased from 1220 grams to 1150 grams.

The sample of Example 1 was placed for 12 hours in a hot-air oven operating at 120° F. (48.9° C). Total weight of the dried article was 84 grams, close to the original weight of the sample. Overall dimensions measured 0.20×12.0×11.2 inches (0.51×30.5×28.4 cm), very close to the original dimensions. Upon re-wetting the sample, the weight increased to 1572 grams (excluding the fabrics). After squeezing the sample by hand, the sample weight was reduced to 1201 grams (again excluding fabric weight). These data indicate that the article is readily reusable.

I claim:

1. An article of manufacture particularly suited for use as a wet compress having an upper and a lower outer layer and containing between the layers a particulate filling material consisting essentially of 5 to 30 percent of super-absorbent polymer and 70 to 95 percent of diluent by total weight of the filling material, a least one of the layers being an elastic water-permeable fabric having a recoverable stretch of at least 50 percent in at least one direction.

2. An article in accordance with claim 1 wherein the recoverable stretch is in the range of 100 to 300% and the fabric has a bendability of no greater than 1¼ centimeters.

3. An article in accordance with claim 2 wherein the bendability is no greater than ¾ cm.

4. An article in accordance with claim 3 wherein the filling material is capable of absorbing 15 to 35 times its weight in water to form a hydrogel and the article when so wetted is capable of swelling to 3 to 10 times its original dry volume.

5. An article in accordance with claim 4 wherein the super-absorbent polymer particles amount to 8 to 15% of the filling material and the diluent is a mixture of wood pulp and polyethylene synthetic pulp.

6. An article in accordance with claim 1, 4 or 5 wherein the elastic water-permeable fabric is a spun-bonded polyolefin fabric that is stitch-bonded with an elastic stitching thread.

7. An article in accordance with claim 1, 4 or 5 wherein the elastic water-permeable fabric is a carded batt of acrylic and polyester staple fibers that is stitch-bonded with an elastic stitching thread.

* * * * *